(12) United States Patent
Qian et al.

(10) Patent No.: US 11,069,261 B2
(45) Date of Patent: Jul. 20, 2021

(54) FOOD SWALLOWING SIMULATING DEVICE

(71) Applicant: Jiangnan University, Wuxi (CN)

(72) Inventors: Shanhua Qian, Wuxi (CN); Baoxing Wang, Wuxi (CN); Di Wang, Wuxi (CN); Zifeng Ni, Wuxi (CN); Jinghu Yu, Wuxi (CN)

(73) Assignee: Jiangnan University, Wuxi (CN)

( * ) Notice: Subject to any disclaimer, the term of this patent is extended or adjusted under 35 U.S.C. 154(b) by 325 days.

(21) Appl. No.: 16/201,017

(22) Filed: Nov. 27, 2018

(65) Prior Publication Data

US 2019/0096288 A1 Mar. 28, 2019

Related U.S. Application Data

(63) Continuation of application No. PCT/CN2017/119417, filed on Dec. 28, 2017.

(30) Foreign Application Priority Data

Jul. 3, 2017 (CN) .......................... 201710531532.1

(51) Int. Cl.
*G09B 23/32* (2006.01)
*G09B 23/28* (2006.01)
(Continued)

(52) U.S. Cl.
CPC ............ *G09B 23/32* (2013.01); *G09B 23/28* (2013.01); *G09B 23/283* (2013.01); *G09B 23/30* (2013.01);
(Continued)

(58) Field of Classification Search
CPC ........ G09B 23/32; G09B 23/34; G09B 23/30; G09B 23/303; G09B 23/28; G09B 23/306;
(Continued)

(56) References Cited

U.S. PATENT DOCUMENTS

2011/0239947 A1* 10/2011 Chang ................. A01K 5/0225
119/52.1
2014/0120224 A1* 5/2014 Kamiya ................... G16B 5/00
426/416
(Continued)

FOREIGN PATENT DOCUMENTS

CN 202887580 U 4/2013
CN 203117187 U 8/2013
(Continued)

*Primary Examiner* — James B Hull
*Assistant Examiner* — Lily M Del Valle
(74) *Attorney, Agent, or Firm* — IPro, PLLC

(57) ABSTRACT

The present invention discloses a food swallowing simulating device, and belongs to the field of structural design of bio-simulation machinery. The device comprises an upper jaw matrix, a tongue matrix, a transmission device and a driving device; the upper jaw matrix and the tongue matrix are arranged oppositely, and opposite surfaces are curved surfaces; a channel is reserved between the curved surfaces to form a bionic oral cavity; and the tongue matrix is connected with the driving device by the transmission device, so that the motion of the tongue matrix is controlled by the driving device. Transition from static food swallowing mechanism simulation to dynamic food swallowing mechanism simulation is realized, and thus, a blank in the market is made up.

19 Claims, 4 Drawing Sheets

(51) Int. Cl.
*G09B 23/30* (2006.01)
*G09B 23/34* (2006.01)
*A61B 5/00* (2006.01)
*G09B 23/00* (2006.01)
*A61B 17/00* (2006.01)

(52) U.S. Cl.
CPC ... *A61B 5/4205* (2013.01); *A61B 2017/00707* (2013.01); *A61B 2505/09* (2013.01); *G09B 23/00* (2013.01); *G09B 23/303* (2013.01); *G09B 23/306* (2013.01); *G09B 23/34* (2013.01)

(58) Field of Classification Search
CPC .................. G09B 23/00; G09B 23/283; A61B 2017/00707; A61B 2505/09; A61B 5/4205
USPC .......................... 434/272, 274, 267, 262, 270
See application file for complete search history.

(56) References Cited

U.S. PATENT DOCUMENTS

| | | | | |
|---|---|---|---|---|
| 2014/0272875 A1* | 9/2014 | Francois | ................ | G09B 23/32 434/270 |
| 2015/0079570 A1* | 3/2015 | Michiwaki | ............. | G09B 23/28 434/270 |
| 2015/0132723 A1* | 5/2015 | Evans | .................... | G16H 20/60 434/127 |
| 2018/0012515 A1* | 1/2018 | Loan | ......................... | G09B 9/00 |
| 2019/0021536 A1* | 1/2019 | Zhou | ....................... | A47J 19/00 |
| 2019/0333414 A1* | 10/2019 | Nakano | .................... | G09B 9/00 |

FOREIGN PATENT DOCUMENTS

| | | |
|---|---|---|
| CN | 103426350 A | 12/2013 |
| CN | 206057269 U | 3/2017 |
| CN | 107154208 A | 9/2017 |

* cited by examiner

FOOD SWALLOWING SIMULATING DEVICE

TECHNICAL FIELD

The present disclosure relates to a food swallowing simulating device, and belongs to the field of structural design of bio-simulation machinery.

BACKGROUND

Dysphagia is a common complication after stroke of the elderly, feeding relatively safe food according to the severity of dysphagia of different patients by improving the material characteristics of food is a means for treating dysphagia. However, food flowing during swallowing and in-vivo measurement data of a swallowing system cannot be acquired easily due to complexity of the structure of the swallowing system of a human body, therefore, an oral cavity food swallowing simulating device is provided, an in-vitro test environment is provided for researching the flowing characteristics of food after the food is swallowed, and the oral cavity food swallowing simulating device has great significance on promotion of improvement of the living quality of patients with dysphagia and research and treatment of the dysphagia.

Existing swallowing device models have comparatively outstanding medical industrial characteristics, most of the existing swallowing device models are static structural models, a swallowing process cannot be demonstrated dynamically, thus, measurement data which play an important role in disease treatment and development of safe food cannot be acquired effectively by existing devices, and research on influence of material characteristics of food to a swallowing process and development of related effective food cannot be propelled effectively.

SUMMARY

The present disclosure provides a food swallowing simulating device which comprises a bionic oral cavity, a feeding device, a transmission device and a driving device; the bionic oral cavity comprises an upper jaw matrix and a tongue matrix, the upper jaw matrix covers the tongue matrix inside, a recessed curved surface is arranged in the upper jaw matrix, a protruded curved surface is arranged on the upper portion of the tongue matrix, and the recessed curved surface and the protruded curved surface separately simulate a curved surface on which an oral cavity upper jaw is located and a curved surface on which the surface of a tongue is located; a channel for food to pass through is reserved between the opposite curved surfaces of the upper jaw matrix and the tongue matrix; one end of the feeding device is communicated with the channel of the bionic oral cavity while the other end is connected with the transmission device; and the transmission device is separately connected with the tongue matrix and the feeding device, and is used for driving the tongue matrix and the feeding device to move synchronously under the effect of the driving device.

In one embodiment of the present disclosure, the feeding device comprises a ball pushing rod, a funnel and a stock bin; and a three-way channel is formed in the stock bin, a vertical channel is connected with the funnel, two ends of a transverse channel separately serve as a connecting port with the bionic oral cavity and an inlet of the ball pushing rod, the ball pushing rod is connected with the transmission device, and piston motion is did in the transverse channel in the stock bin.

In one embodiment of the present disclosure, the driving device comprises a motor, a coupler and a rotating shaft; the motor is connected with the rotating shaft through the coupler; and a crank and the coupler are separately mounted at two ends of the rotating shaft.

In one embodiment of the present disclosure, the driving device comprises a motor, a coupler, a rotating shaft, a mounted bearing and a crank; the rotating shaft is fixed in the mounted bearing, and the crank and the coupler are separately mounted at two ends of the rotating shaft; and the motor is connected with the rotating shaft through the coupler.

In one embodiment of the present disclosure, the transmission device comprises a transmission connecting block, a gear, a rack, a crank and a transmission rod; the transmission connecting block is connected with the tongue matrix; the transmission connecting block and the gear are coaxially arranged; the rack is engaged with the gear and is separately connected with the transmission rod and an oscillating rod of the crank; and the transmission rod is connected with the ball pushing rod.

In one embodiment of the present disclosure, the rack is connected with the transmission rod and the oscillating rod of the crank through an E-shaped connecting piece; and the E-shaped connecting piece is fixed at an end of the rack, and is provided with two grooves, one groove serves as a fulcrum of the oscillating rod while the other groove is used for fixing the transmission rod, and thus, the transmission rod and the rack are connected to form an integrated structure.

In one embodiment of the present disclosure, the transmission device comprises a first mounted bearing, a second mounted bearing, a first rotating shaft, a transmission connecting block, a gear, a second rotating shaft, a square connecting rod, a rack, a first sliding block, linear guide rails, a second sliding block, an L-shaped transmission rod and a crank; the first mounted bearing and the second mounted bearing are coaxially arranged, and the first rotating shaft is inserted in the first mounted bearing and the second mounted bearing in a penetrating manner; the gear and the transmission connecting block are coaxially arranged on the first rotating shaft, and the tongue matrix and the first rotating shaft are fixed by the transmission connecting block; the rack which can be engaged with the gear is arranged below the gear; the linear guide rails are arranged below the rack in parallel; the first sliding block and the second sliding block which slide are arranged on the linear guide tracks; the rack is supported by first sliding block; and the L-shaped transmission rod is supported by the second sliding block.

In one embodiment of the present disclosure, a soft tissue material covers the curved surface of the upper jaw matrix; and the soft tissue material includes but not limited to rubber and silica gel.

In one embodiment of the present disclosure, the linear guide rails are fixed on a bottom plate, and are positioned between the first mounted bearing and the second mounted bearing.

In one embodiment of the present disclosure, miniature sensing sheets are separately arranged on two curved surfaces which form the channel of the bionic oral cavity.

A second object of the present disclosure is to provide a method for analyzing food, and the food swallowing simulating device is used for simulating swallowing so as to analyze materials, sizes, hardness or viscosity of the food.

The present disclosure has the following beneficial effects: (1) the transition from static food swallowing mechanism simulation to dynamic food swallowing mechanism simulation is realized, a blank in the market is made up, and the innovativeness is high; (2) the rotational motion of the motor is transformed into the reciprocating linear motion of the rack by the device of the present disclosure, the reciprocating linear motion of the rack is transformed into the reciprocating oscillating of the tongue matrix by a gear and rack pair, and the tongue matrix which oscillates in a reciprocating manner may extrude the food step by step, and finally, a swallowing process is completed; (3) continuous food swallowing can be realized, the automatic feeding device and the swallowing action of a tongue form internal-correlative transmission so that a material is fed automatically once every time when the tongue oscillates to a feeding position, the automatic feeding device of the device is connected with the rack to transmit the reciprocating motion of the rack to the pushing rod, so as to guarantee that the material is automatically fed once every time when the tongue oscillates once; (4) the simulating device in the present disclosure is simple in structure and convenient to operate, a measuring device is additionally arranged in the bionic oral cavity of the device favorably, and effective related data can be provided for related food and medical industries; and (5) structural machinability of parts is good, and feasibility of processing and manufacturing is high.

DETAILED DESCRIPTION

Figure 1:
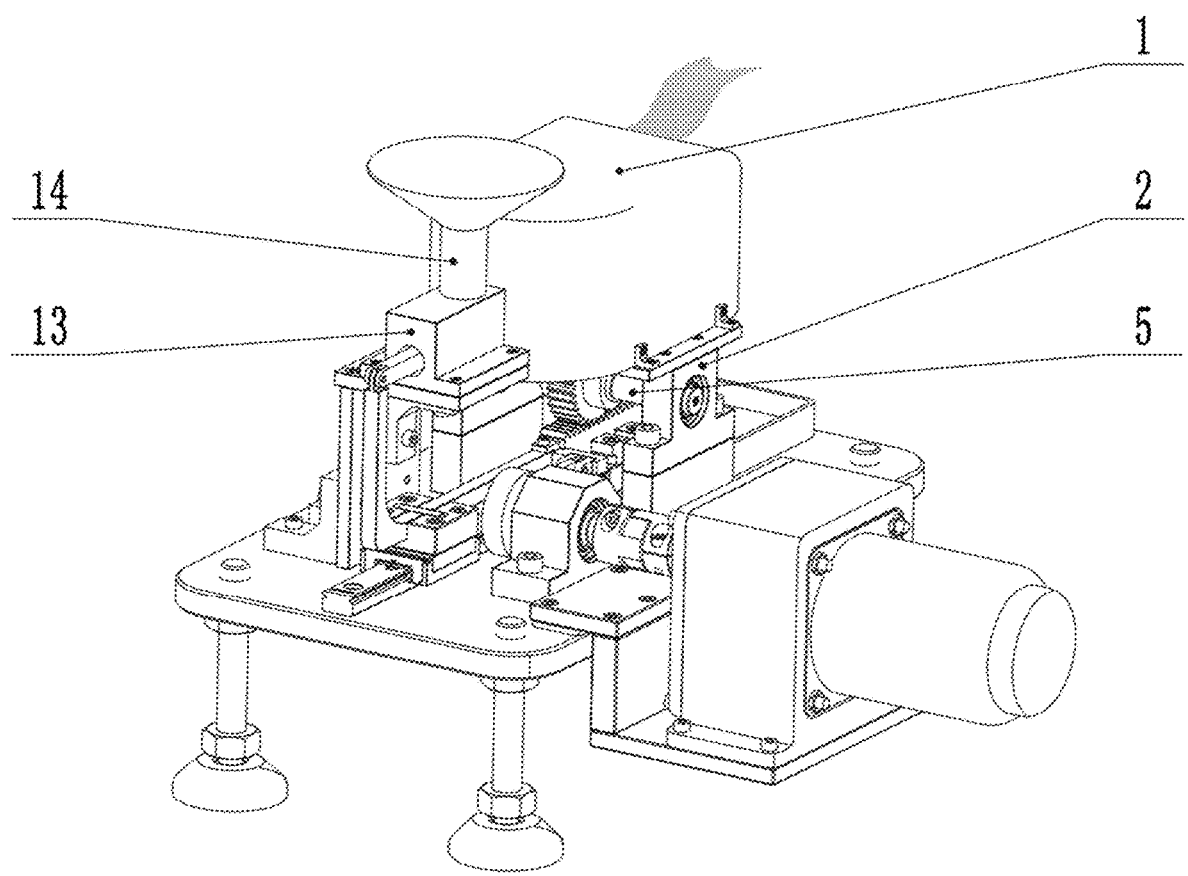
FIG. 1 is a structural schematic diagram of one embodiment of the present disclosure.
Figure 2:
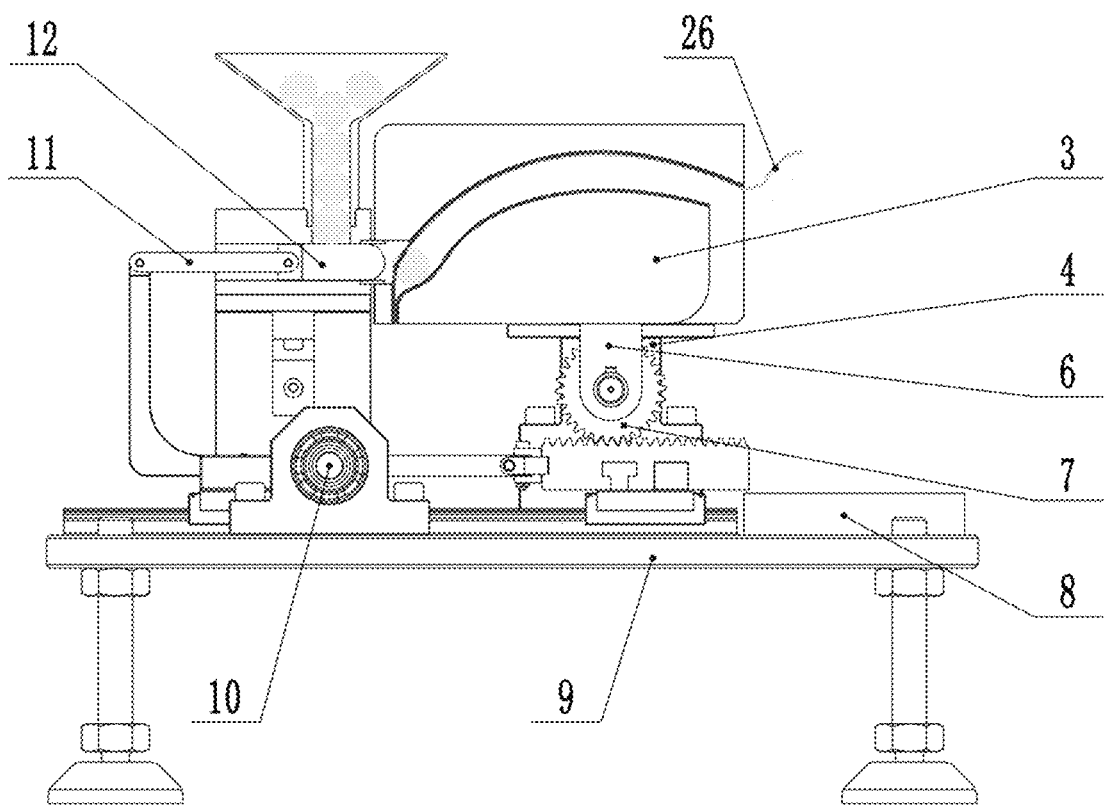
FIG. 2 is a structural schematic diagram of a transmission device of one embodiment of the present disclosure.
Figure 3:
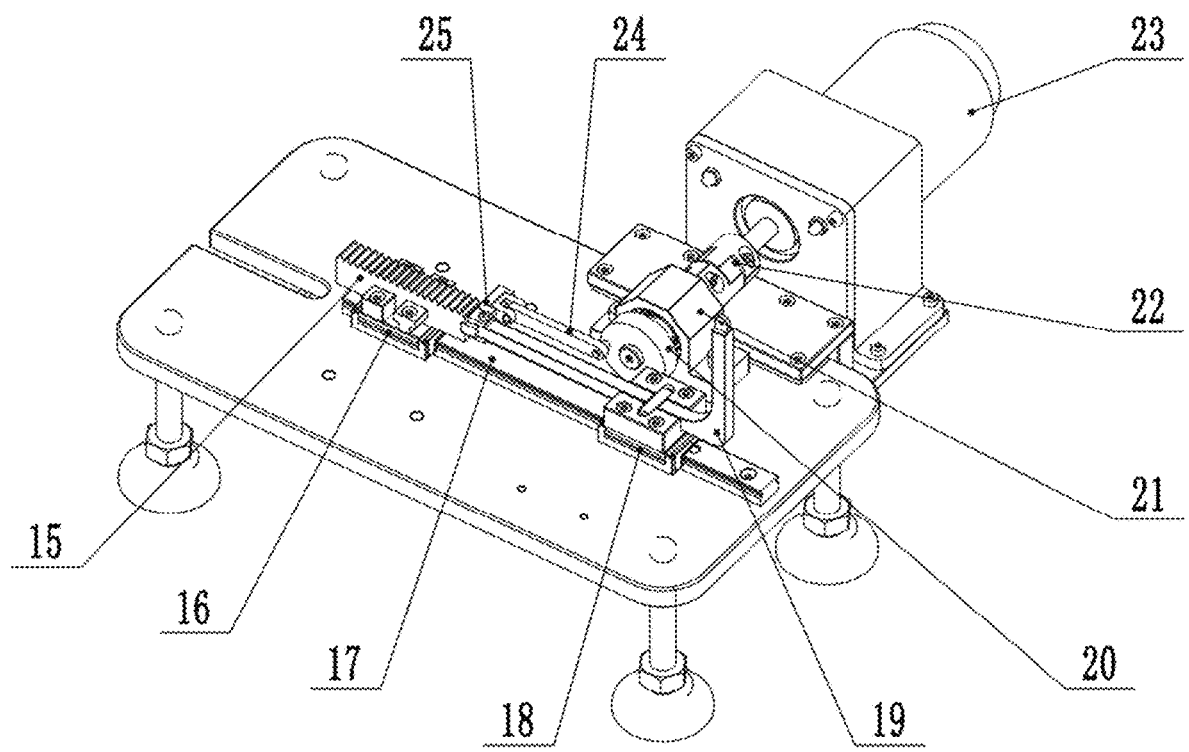
FIG. 3 is a structural schematic diagram of a crank and sliding block device of one embodiment of the present disclosure.
Figure 4:
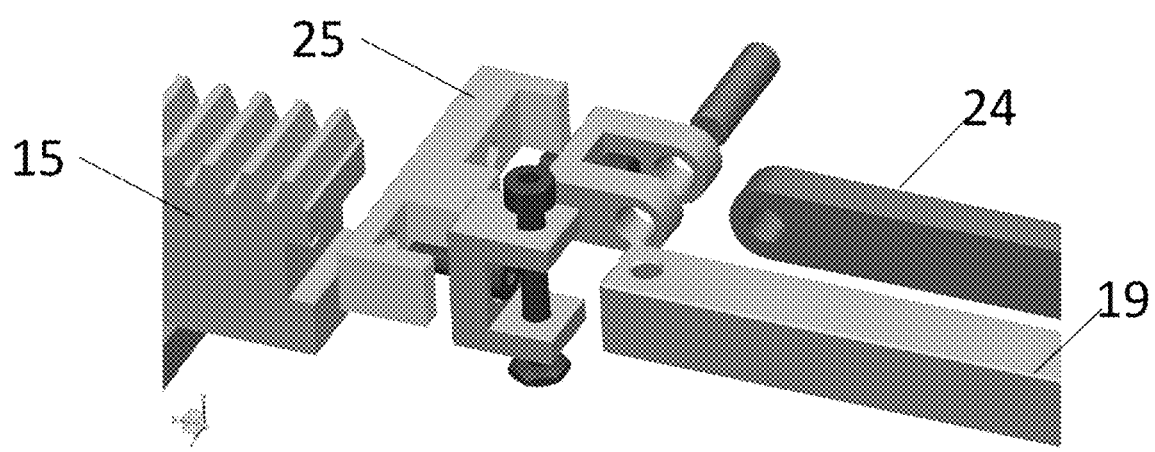
FIG. 4 is a partial enlarged view of an E-shaped connecting piece in a mechanical device of the present disclosure.

As shown in FIGS. 1 to 3, a food swallowing simulating device comprises an upper jaw matrix 1, a tongue matrix 3, a feeding device, a transmission device and a driving device; the upper jaw matrix 1 covers the tongue matrix 3 inside, a recessed curved surface is arranged in the upper jaw matrix 1, a protruded curved surface is arranged on the upper portion of the tongue matrix 3, and the recessed curved surface and the protruded curved surface separately simulate a curved surface on which an oral cavity upper jaw is located and a curved surface on which the surface of a tongue is located; and a channel for food to pass through is reserved between opposite curved surfaces of the upper jaw matrix 1 and the tongue matrix 3 to form a bionic oral cavity.

Soft tissue materials cover the internal curved surface of the upper jaw matrix 1 and the curved surface of the tongue matrix 3, and include but not limited to rubber and silica gel. On the two curved surfaces which form the channel of the bionic oral cavity, miniature sensing sheets 26 are arranged on the surface of at least one soft tissue material, and are used for measuring pressure in a swallowing process. The upper jaw matrix 1 is fixed above the first mounted bearing 2 and the second mounted bearing 4 through corner bars, and bearing blocks of the first mounted bearing 2 and the second mounted bearing 4 are fixed on a bottom plate 9.

The first mounted bearing 2 and the second mounted bearing 4 are coaxially arranged, and a first rotating shaft 5 is inserted in the first mounted bearing 2 and the second mounted bearing 4 in a penetrating manner. A gear 7 and a transmission connecting block 6 are coaxially arranged on the first rotating shaft 5, and the tongue matrix 3 and the first rotating shaft 5 are fixed by the transmission connecting block 6 so that the tongue matrix 3 rotates around the first rotating shaft 5; and a rack 15 which can be engaged with the gear 7 is arranged below the gear 7. Linear guide rails 17 are arranged below the rack 15 in parallel, are fixed on the bottom plate 9, and are positioned in a region between the first mounted bearing 2 and the second mounted bearing 4. The linear guide rails 17 are provided with a first sliding block 16 and a second sliding block 17 which can slide along the linear guide rails 17; the rack 15 is supported by the first sliding block 16; and the L-shaped transmission rod 19 is supported by the second sliding block 17. A groove is formed in the end surface of one end of the rack 7, and an E-shaped connecting piece 25 is fixed in the groove of the end surface of the rack 15. The E-shaped connecting piece 25 is provided with two grooves, and one groove serves as a fulcrum of an oscillating rod 24 and is connected with the oscillating rod 24 in a riveted manner; and the other groove is used for fixing the L-shaped transmission rod 19 so that the L-shaped transmission rod 19 and the rack 15 form an integrated structure.

The other end of the oscillating rod 24 and the plane of a crank 20 are fixed by clearance fit between a cylindrical pin arranged on the crank 20 and a pin hole formed in the other end of the oscillating rod 24, the crank 20 is arranged at one end of a second rotating shaft 10, and the second rotating shaft 10 is fixed in a third mounted bearing 21 and is connected with a coupler 22; and a motor 23 is connected with the second rotating shaft 10 through the coupler 22. The motor 23 drives the second rotating shaft 10 to rotate, the crank 20 is driven to rotate by the second rotating shaft 10, and the other end, which is connected with the E-shaped connecting piece, of the oscillating rod 24 does linear reciprocating motion under the rotation of the crank. The third mounted bearing 21 is fixed on the bottom plate 9 through a bearing block.

The present disclosure further comprises a stock bin 13, a funnel 14, a ball pushing rod 12 and a collecting box 8. The stock bin 13 is positioned on the side, which is provided with a feeding hole, of the upper jaw matrix 1, and the stock bin 13 is provided with a three-way channel; a transverse end of the channel is an inlet duct, and is communicated with the channel between the upper jaw matrix 1 and the tongue matrix 3, the other end is inserted in the ball pushing rod 12 so that the ball of the ball pushing rod 12 faces the region in which the tongue matrix 3 is located, and the other end of the ball pushing rod 12 is connected with one end of a square connecting rod 11; and the other end of the square connecting rod 11 is connected with an end of an L-shaped transmission rod 19, and does the same transverse linear reciprocating motion under the action of the L-shaped transmission rod 19, and the ball pushing rod 12 is pushed to do reciprocating piston motion in the transverse channel of the three-way channel so as to push the food bolus which enters from the funnel 14 into the channel of the bionic oral cavity. The other end of the channel is a food bolus outlet, and the collecting box 8 is arranged just under the outlet and is used for collecting food boluses.

Figure 5:
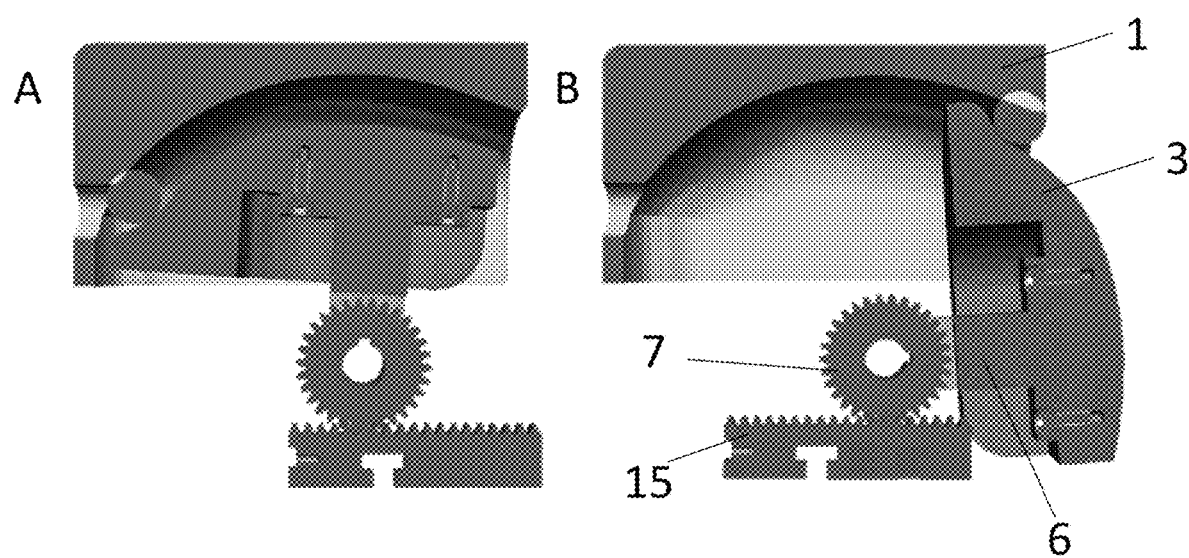
FIG. 5 is a schematic diagram of a motion mode of a food bolus in a swallowing device of the present disclosure; A, the food bolus just enters the swallowing device; B, the food bolus moves to an outlet of a channel by the effect of the swallowing device; wherein 1, upper jaw matrix; 2, first mounted bearing; 3, tongue matrix; 4, second mounted bearing; 5, first rotating shaft; 6, transmission connecting block; 7, gear; 8, collecting box; 9, bottom plate; 10, second rotating shaft; 11, square connecting rod; 12, ball pushing rod; 13, stock bin; 14, funnel; 15, rack; 16, first sliding block; 17, linear guide rail; 18, second sliding block; 19, L-shaped transmission rod; 20, crank; 21, third mounted bearing; 22, coupler; 23, motor; 24, oscillating rod; 25, E-shaped connecting piece; and 26, miniature sensing sheet.

As shown in FIG. 5, the working principle of the present disclosure is as follows: a spherical food bolus of which the diameter does not exceed the aperture of the funnel is placed in the funnel 14, and after the motor 23 is electrified, the crank 20 revolves and drives the rack 15 and the pushing rod 12 to do reciprocating linear motion along the linear guide rails 17. When the crank 20 drives the oscillating rod 24 to drive the rack 15 to do reciprocating linear motion, the reciprocating linear motion is transmitted to the ball pushing rod from the rack 15 via the L-shaped transmission rod 19 and the square connecting rod 11. Because the tongue matrix 3 and the gear 7 are fixed on the first rotating shaft 5 together through the transmission connecting block 6, when the gear 7 is engaged with the rack 15 and the rack 15 does reciprocating linear motion, the tongue matrix 3 oscillates in a reciprocating manner, and under the limitation of the maximum radial motion displacement of the oscillating rod 24 on the crank 20, the oscillating angle of the tongue matrix 3 is about 90 degrees. Under the driving effect of the rack 15, the ball pushing rod 12 does reciprocating linear motion in the transverse channel of the three-way channel via motion transmission of the L-shaped transmission rod 19 and the square connecting rod 11, thus, swallowing action and pushing action form internal-correlative transmission, every time when the tongue matrix 3 oscillates to the feeding position, the pushing rod 12 may automatically push the food bolus into the bionic oral cavity once, thus, the food bolus is extruded in the bionic oral cavity step by step and finally slips into the collecting box 8, and a whole food swallowing process in the oral cavity is finished. The miniature sensing sheets 26 are arranged on the opposite curved surfaces of the upper jaw matrix 1 and the tongue matrix 3, pressure in the swallowing process can be measured to evaluate the difficulty level of the food boluses with different materials, sizes, hardness and viscosity in the swallowing process, and a method for researching development of safe food is provided.

What is claimed is:

1. A simulating device for food swallowing, comprising a bionic oral cavity, a feeding device, a transmission device and a driving device;
    wherein the bionic oral cavity comprises an upper jaw matrix and a tongue matrix, the upper jaw matrix covers the tongue matrix inside, a recessed curved surface is arranged in the upper jaw matrix, a protruded curved surface is arranged on an upper portion of the tongue matrix, and the recessed curved surface and the protruded curved surface separately simulate a curved surface on which an oral cavity upper jaw is located and a curved surface on which a surface of a tongue is located;
    wherein a channel for food to pass through is reserved between opposite curved surfaces of the upper jaw matrix and the tongue matrix;
    wherein one end of the feeding device is communicated with the channel of the bionic oral cavity while the other end is connected with the transmission device;
    wherein the transmission device is separately connected with the tongue matrix and the feeding device, and is used for driving the tongue matrix and the feeding device to move synchronously under driving effect of the driving device;
    wherein the transmission device comprises a transmission connecting block, a gear, a rack, a crank and a transmission rod;
    wherein the transmission connecting block is connected with the tongue matrix;
    wherein the transmission connecting block and the gear are coaxially arranged;
    wherein the rack is engaged with the gear, and is separately connected with the transmission rod and an oscillating bar of the crank;
    wherein the transmission rod is connected with a ball pushing rod;
    wherein the rack is connected with the transmission rod and oscillating rod of the crank by an E-shaped connecting piece; and
    wherein the E-shaped connecting piece is fixed at an end of the rack and is provided with two grooves, one groove serves as a fulcrum of the oscillating rod while the other groove is used for fixing the transmission rod, and thus, the transmission rod and the rack are connected to form an integrated structure.

2. The simulating device according to claim 1, wherein the feeding device comprises a ball pushing rod, a funnel and a stock bin; and
    wherein a three-way channel is formed in the stock bin, a vertical channel is connected with the funnel, two ends of a transverse channel separately serve as a connecting port with the bionic oral cavity and an inlet of the ball pushing rod, and the ball pushing rod is positioned in the transverse channel and is connected with the transmission device.

3. The simulating device according to claim 2, wherein a soft tissue material covers the curved surface of the upper jaw matrix; and
    wherein the soft tissue material comprises rubber or silica gel.

4. The simulating device according to claim 1, wherein the driving device comprises a motor, a coupler and a rotating shaft;
    wherein the motor is connected with the rotating shaft through the coupler; and
    wherein a crank and the coupler are separately mounted at two ends of the rotating shaft.

5. The simulating device according to claim 4, wherein a soft tissue material covers the curved surface of the upper jaw matrix; and the soft tissue material comprises rubber or silica gel.

6. The simulating device according to claim 1, wherein a soft tissue material covers the curved surface of the upper jaw matrix; and
    wherein the soft tissue material comprises rubber or silica gel.

7. The simulating device according to claim 1, wherein a soft tissue material covers the curved surface of the upper jaw matrix; and
    wherein the soft tissue material comprises rubber or silica gel.

8. The simulating device according to claim 1, wherein a soft tissue material covers the curved surface of the upper jaw matrix; and wherein the soft tissue material comprises rubber or silica gel.

9. The simulating device according to claim 1, wherein miniature sensing sheets are separately arranged on two curved surfaces which form the channel of the bionic oral cavity.

10. A simulating device for food swallowing, comprising a bionic oral cavity, a feeding device, a transmission device and a driving device;

wherein the bionic oral cavity comprises an upper jaw matrix and a tongue matrix, the upper jaw matrix covers the tongue matrix inside, a recessed curved surface is arranged in the upper jaw matrix, a protruded curved surface is arranged on an upper portion of the tongue matrix, and the recessed curved surface and the protruded curved surface separately simulate a curved surface on which an oral cavity upper jaw is located and a curved surface on which a surface of a tongue is located;

wherein a channel for food to pass through is reserved between opposite curved surfaces of the upper jaw matrix and the tongue matrix;

wherein one end of the feeding device is communicated with the channel of the bionic oral cavity while the other end is connected with the transmission device;

wherein the transmission device is separately connected with the tongue matrix and the feeding device, and is used for driving the tongue matrix and the feeding device to move synchronously under driving effect of the driving device;

wherein the transmission device comprises a transmission connecting block, a gear, a rack, a crank and a transmission rod;

wherein the transmission connecting block is connected with the tongue matrix;

wherein the transmission connecting block and the gear are coaxially arranged;

wherein the rack is engaged with the gear, and is separately connected with the transmission rod and an oscillating bar of the crank;

wherein the transmission rod is connected with a ball pushing rod;

wherein the transmission device comprises a first mounted bearing, a second mounted bearing, a first rotating shaft, a transmission connecting block, a gear, a square connecting rod, a rack, a first sliding block, linear guide rails, a second sliding block, an L-shaped transmission rod and a crank;

wherein the first mounted bearing and the second mounted bearing are coaxially arranged, and the first rotating shaft is inserted in the first mounted bearing and the second mounted bearing in a penetrating manner;

wherein the gear and the transmission connecting block are coaxially arranged on the first rotating shaft, and the tongue matrix and the first rotating shaft are fixed by the transmission connecting block;

wherein the rack which can be engaged with the gear is arranged below the gear; the linear guide rails are arranged below the rack in parallel;

wherein the first sliding block and the second sliding block which are slidable are arranged on the linear guide rails;

wherein the rack is supported by the first sliding block; and wherein the L-shaped transmission rod is supported by the second sliding block.

11. The simulating device according to claim 10, wherein a soft tissue material covers the curved surface of the upper jaw matrix; and wherein the soft tissue material comprises rubber or silica gel.

12. The simulating device according to claim 10, wherein the linear guide rails are fixed on a bottom plate and are positioned between the first mounted bearing and the second mounted bearing.

13. The simulating device according to claim 10, wherein the feeding device comprises a ball pushing rod, a funnel and a stock bin; and wherein a three-way channel is formed in the stock bin, a vertical channel is connected with the funnel, two ends of a transverse channel separately serve as a connecting port with the bionic oral cavity and an inlet of the ball pushing rod, and the ball pushing rod is positioned in the transverse channel and is connected with the transmission device.

14. The simulating device according to claim 13, wherein a soft tissue material covers the curved surface of the upper jaw matrix; and wherein the soft tissue material comprises rubber or silica gel.

15. The simulating device according to claim 10, wherein the driving device comprises a motor, a coupler and a rotating shaft;

wherein the motor is connected with the rotating shaft through the coupler; and wherein a crank and the coupler are separately mounted at two ends of the rotating shaft.

16. The simulating device according to claim 15, wherein a soft tissue material covers the curved surface of the upper jaw matrix; and the soft tissue material comprises rubber or silica gel.

17. The simulating device according to claim 10, wherein a soft tissue material covers the curved surface of the upper jaw matrix; and wherein the soft tissue material comprises rubber or silica gel.

18. The simulating device according to claim 10, wherein a soft tissue material covers the curved surface of the upper jaw matrix; and wherein the soft tissue material comprises rubber or silica gel.

19. The simulating device according to claim 10, wherein miniature sensing sheets are separately arranged on two curved surfaces which form the channel of the bionic oral cavity.

* * * * *